US011734981B2

(12) United States Patent
Ouellette et al.

(10) Patent No.: US 11,734,981 B2
(45) Date of Patent: Aug. 22, 2023

(54) ENHANCED ENTRY AUTHORIZATION

(71) Applicant: Johnson Controls Tyco IP Holdings LLP, Milwaukee, WI (US)

(72) Inventors: Jason M. Ouellette, Sterling, MA (US); Allen Houston, Lisburn (GB); David S. Pinney, Westford, MA (US); Lipphei Adam, Nolensville, TN (US)

(73) Assignee: Johnson Controls Tyco IP Holdings LLP, Milwaukee, WI (US)

(*) Notice: Subject to any disclaimer, the term of this patent is extended or adjusted under 35 U.S.C. 154(b) by 192 days.

(21) Appl. No.: 17/143,693

(22) Filed: Jan. 7, 2021

(65) Prior Publication Data

US 2022/0068070 A1 Mar. 3, 2022

Related U.S. Application Data

(60) Provisional application No. 63/074,350, filed on Sep. 3, 2020.

(51) Int. Cl.
*G07C 11/00* (2006.01)
*G07C 9/10* (2020.01)

(52) U.S. Cl.
CPC .............. *G07C 11/00* (2013.01); *G07C 9/10* (2020.01); *G07C 2209/14* (2013.01)

(58) Field of Classification Search
CPC ...... G07C 11/00; G07C 9/10; G07C 2209/14; G07C 9/30; G07C 9/27; G07C 9/33; G07C 9/37; A61B 5/015; G06Q 50/265
USPC ........................................................ 340/5.52
See application file for complete search history.

(56) References Cited

U.S. PATENT DOCUMENTS

| 10,720,001 | B1 * | 7/2020 | Grosberg ................. G07C 9/27 |
| 2006/0206724 | A1 * | 9/2006 | Schaufele .............. G07C 9/257 726/16 |
| 2017/0018007 | A1 * | 1/2017 | DeFrank ................ G16H 50/20 |
| 2019/0043605 | A1 * | 2/2019 | Hegarty ............... A61B 5/4833 |

(Continued)

FOREIGN PATENT DOCUMENTS

| KR | 20170083842 A | 7/2017 |
| KR | 102135633 B1 | 8/2020 |
| WO | 2011/005224 A1 | 1/2011 |

OTHER PUBLICATIONS

European Search Report dated Feb. 1, 2002 received in corresponding EP Application No. 21194815.3.

*Primary Examiner* — Omar Casillashernandez
(74) *Attorney, Agent, or Firm* — Arentfox Schiff LLP

(57) ABSTRACT

Disclosed herein are apparatuses and methods for granting entry through a checkpoint. The implementations include receiving a request for entry of a person through a checkpoint. The implementations include estimating, via a thermal sensor, a body surface temperature of the person, and generating, via a user interface, a notification that prompts the person to answer at least one verification question. The implementations include receiving, via the user interface, at least one user response to the at least one verification question. The implementations include determining whether the at least one user response and the body surface temperature match criteria for gaining entry through the checkpoint. Additionally, the implementations include granting the request for entry in response to determining that the at least one user response and the body surface temperature match the criteria.

14 Claims, 5 Drawing Sheets

(56) References Cited

U.S. PATENT DOCUMENTS

| | | | |
|---|---|---|---|
| 2019/0268575 A1* | 8/2019 | Leow | G06K 9/00536 |
| 2020/0118164 A1* | 4/2020 | DeFrank | G06Q 30/0269 |
| 2021/0304537 A1* | 9/2021 | Reed | G06K 9/6201 |
| 2021/0327187 A1* | 10/2021 | Wisniewski | G16H 10/20 |
| 2021/0335072 A1* | 10/2021 | Caldwell | G07C 9/00563 |
| 2021/0369122 A1* | 12/2021 | Lane | G01J 5/0275 |
| 2021/0375084 A1* | 12/2021 | Aubrey | G07C 9/27 |
| 2021/0390812 A1* | 12/2021 | Chaurasia | G07C 9/22 |
| 2022/0018715 A1* | 1/2022 | Moton, Jr. | G06V 40/166 |
| 2022/0076517 A1* | 3/2022 | Haddad | G07C 9/38 |

\* cited by examiner

ENHANCED ENTRY AUTHORIZATION

CROSS-REFERENCE TO RELATED APPLICATIONS

This application claims the benefit of U.S. Provisional Application No. 63/074,350, filed Sep. 3, 2020, which is herein incorporated by reference.

TECHNICAL FIELD

The described aspects relate to security systems.

BACKGROUND

Aspects of the present disclosure relate generally to security systems, and more particularly, to granting entry through a checkpoint.

In certain facilities and environments, enhanced security measures are needed to ensure that only authorized individuals are allowed entry. Depending on the circumstances, however, even individuals that would normally be allowed entry, may need to be denied access.

Accordingly, there exists a need for improvements in security systems.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

An example implementation includes a method for granting entry through a checkpoint, comprising receiving a request for entry of a person through a checkpoint. In response to receiving the request for entry, the method further includes estimating, via a thermal sensor, a body surface temperature of the person and generating, via a user interface, a notification that prompts the person to answer at least one verification question. Additionally, the method further includes receiving, via the user interface, at least one user response to the at least one verification question. The method further includes determining whether the at least one user response and the body surface temperature match criteria for gaining entry through the checkpoint. Additionally, the method further includes granting the request for entry in response to determining that the at least one user response and the body surface temperature match the criteria.

Another example implementation includes an apparatus for granting entry through a checkpoint, comprising a memory and a processor in communication with the memory. The processor is configured to receive a request for entry of a person through a checkpoint. In response to receiving the request for entry, the processor is configured to estimate, via a thermal sensor, a body surface temperature of the person, and generate, via a user interface, a notification that prompts the person to answer at least one verification question. The processor is configured to receive, via the user interface, at least one user response to the at least one verification question. The processor is configured to determine whether the at least one user response and the body surface temperature match criteria for gaining entry through the checkpoint. The processor is configured to, in response to determining that the at least one user response and the body surface temperature match the criteria, grant the request for entry.

Another example implementation includes an apparatus for granting entry through a checkpoint, comprising means for receiving a request for entry of a person through a checkpoint. The apparatus further includes means for estimating, via a thermal sensor, a body surface temperature of the person and generating, via a user interface, a notification that prompts the person to answer at least one verification question in response to receiving the request for entry. Additionally, the apparatus further includes means for receiving, via the user interface, at least one user response to the at least one verification question. Additionally, the apparatus further includes means for determining whether the at least one user response and the body surface temperature match criteria for gaining entry through the checkpoint. Additionally, the apparatus further includes means for in response to determining that the at least one user response and the body surface temperature match the criteria, granting the request for entry.

Another example implementation includes a computer-readable medium for granting entry through a checkpoint, executable by a processor to receive a request for entry of a person through a checkpoint. The instructions are further executable to estimate, via a thermal sensor, a body surface temperature of the person and generate, via a user interface, a notification that prompts the person to answer at least one verification question in response to receiving the request for entry. Additionally, the instructions are further executable to receive, via the user interface, at least one user response to the at least one verification question. Additionally, the instructions are further executable to determine whether the at least one user response and the body surface temperature match criteria for gaining entry through the checkpoint. Additionally, the instructions are further executable to, in response to determining that the at least one user response and the body surface temperature match the criteria, grant the request for entry.

To the accomplishment of the foregoing and related ends, the one or more aspects comprise the features hereinafter fully described and particularly pointed out in the claims. The following description and the annexed drawings set forth in detail certain illustrative features of the one or more aspects. These features are indicative, however, of but a few of the various ways in which the principles of various aspects may be employed, and this description is intended to include all such aspects and their equivalents.

BRIEF DESCRIPTION OF THE DRAWINGS

The accompanying drawings, which are incorporated into and constitute a part of this specification, illustrate one or more example aspects of the present disclosure and, together with the detailed description, serve to explain their principles and implementations.

DETAILED DESCRIPTION

Various aspects are now described with reference to the drawings. In the following description, for purposes of explanation, numerous specific details are set forth in order to provide a thorough understanding of one or more aspects. It may be evident, however, that such aspect(s) may be practiced without these specific details.

The present disclosure includes apparatuses and methods that receive a request from an individual to gain entry through a checkpoint, evaluate the temperature of the individual to detect illness, and query the individual regarding their health status using verification questions to determine whether entry should be granted. For example, during an epidemic or pandemic, offices that normally allow all employees to enter a building may limit access to only healthy employees or employees that have not come in contact with persons with illness. One approach to limiting access may involve having a guard manually assess the health of each incoming employee. However, some buildings may have thousands of employees, with almost all of them trying to enter their offices by a certain time (e.g., 9:00 am). This would make the timely and inefficient manual assessment by an individual, ineffective. Thus, the present disclosure provides a simple and effective solution to providing enhanced access control.

Figure 1:
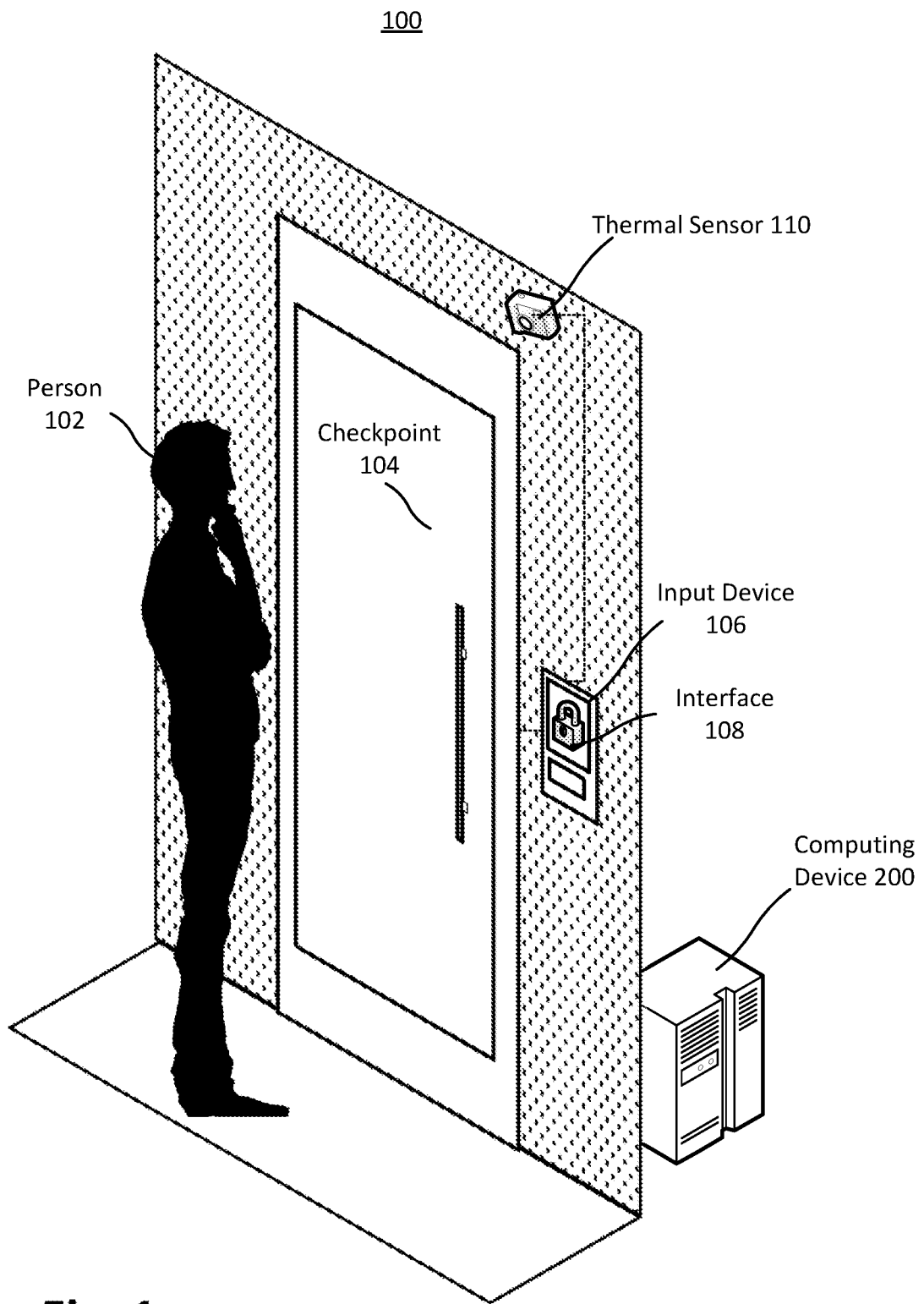
FIG. 1 is a diagram of a scenario for granting entry through a checkpoint, in accordance with exemplary aspects of the present disclosure.

FIG. 1 is a diagram of scenario 100 for granting person 102 entry through checkpoint 104 based upon, at least, received responses to verification questions, such as health-related questions, in accordance with exemplary aspects of the present disclosure. In an example implementation, person 102 may be an employee that is requesting access through checkpoint 104. Checkpoint 104 may be a door, a turnstile, an access point, or any entryway that prevents person 102 from entering. For example, checkpoint 104 may be a locked door to an office. The locking mechanism of checkpoint 104 may be toggled (i.e., lock/unlock) by an electronic control signal from computing device 200 executing an entry authorization component 215 (described in FIGS. 2-4).

Input device 106 may be a peripheral device connected wirelessly (e.g., via Bluetooth, Wi-Fi, Near Field Communications (NFC), etc.) or via a wired connection (e.g., a USB cable) to computing device 200 and configured to receive a user input via an interface 108. In some aspects, input device 106 itself is a standalone computing device capable to executing entry authorization component 215 without computing device 200. Input device 106 may be a touch sensitive display configured to receive a user touch input, a speaker/microphone with a voice recognition module to receive a user voice or audio input, a display/speaker/camera with a gesture recognition module to receive a user gesture input, or a wired or wireless communication device configured to receive an electronic input signal from a communication device (e.g., keyfob, magnetic card, NFC card, radio frequency identification (RFID) device, application of a mobile computer device or phone) of the user (e.g., the person 102). Based on the type of input device 106, interface 108 may be a visual interface and/or an audio-based interface and/or wired or wireless communication interface.

Thermal sensor 110 may be a camera in communication with computing device 200 and/or input device 106. In some aspects, thermal sensor 110 is configured to capture video and images in addition to thermal maps. Thermal sensor 110 may also be a peripheral device of computing device 200.

In combination, computing device 200, input device 106, interface 108, and thermal sensor 110 are utilized to grant/deny entry to person 102 through checkpoint 104 based upon, at least in part, a health status of the person 102.

Figure 2:
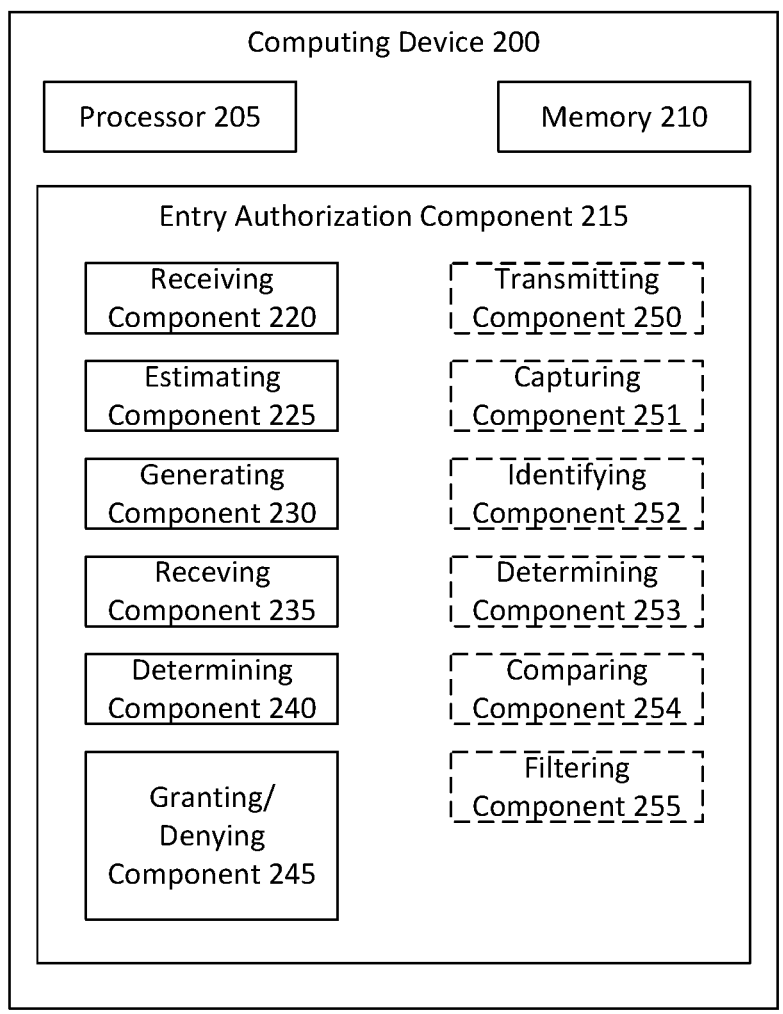
FIG. 2 is a block diagram of a computing device executing an entry authorization component, in accordance with exemplary aspects of the present disclosure.
Figure 3:
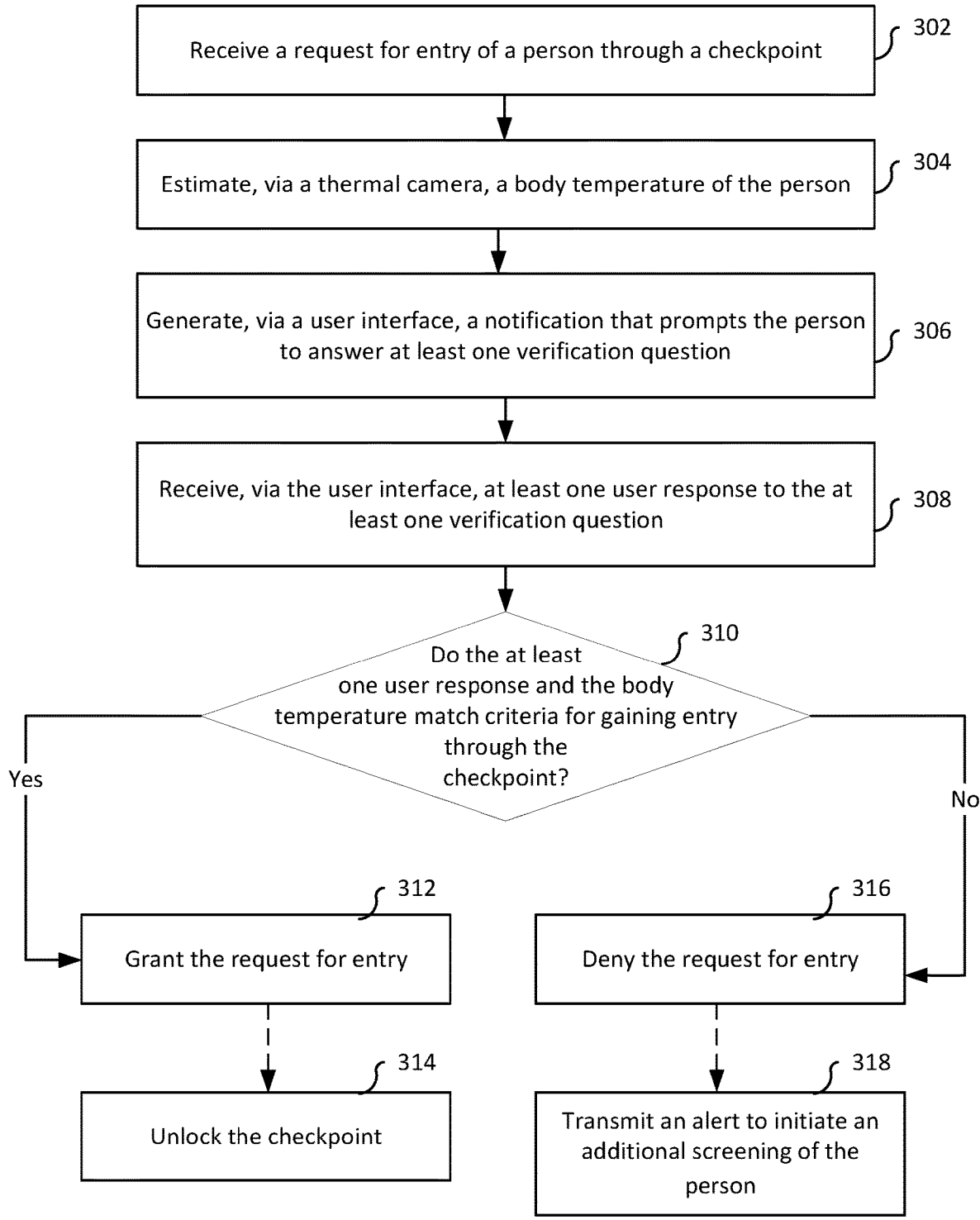
FIG. 3 is a flowchart illustrating a method of granting entry through a checkpoint, in accordance with exemplary aspects of the present disclosure.

FIG. 2 is a block diagram of computing device 200 executing entry authorization component 215, in accordance with exemplary aspects of the present disclosure. FIG. 3 is a flowchart illustrating method 300 of granting entry through a checkpoint, in accordance with exemplary aspects of the present disclosure.

Referring to FIG. 2 and FIG. 3, in operation, computing device 200 may perform method 300 of granting entry through a checkpoint via execution of entry authorization component 215 by processor 205 and/or memory 210.

At block 302, the method 300 includes receiving a request for entry of a person through a checkpoint. For example, in an aspect, computer device 200, processor 205, memory 210, entry authorization component 215, and/or receiving component 220 may be configured to or may comprise means for receiving a request for entry of person 102 through checkpoint 104.

In some aspects, the request for entry may be received via input device 106. For example, receiving component 220 may receive entry credentials of person 102 (which represent the request) via input device 106 at checkpoint 104. In one implementation, person 102 may scan an identification card, a QR code, or an NFC tag, at input device 106, which may be an magnetic stripe reader, a scanner, an NFC reader, etc. In other implementations, input device 106 may be a touch pad and the entry credential may be a fingerprint or alphabetic and/or numeric code. In other implementations, the entry credential may be a voice input captured by a microphone of input device 106. In other implementations, input device 106 may work in conjunction with an external or built-in camera to acquire credentials, including biometric information such as but not limited to a facial image or a retina scan of person 102. In other implementations, input device 106 may detect a personal device of person 102 within a threshold distance from input device 106, which triggers the request. It should be noted that the request may be denied if the access credentials are invalid (e.g., person 102 is not an employee of the office).

At block 304, the method 300 includes estimating, via a thermal sensor, a body surface temperature of the person. For example, in an aspect, computer device 200, processor 205, memory 210, entry authorization component 215, and/or estimating component 225 may be configured to or may comprise means for estimating, via a thermal sensor, a body surface temperature of the person.

For example, thermal sensor 110 may be configured to capture a thermal map of an area on or in contact with a person 102 and output a temperature indicative of the external (e.g., skin) temperature of person 102. This temperature may be transmitted to computing device 200. Suppose that in scenario 100, the temperature is 97.5 degrees Fahrenheit.

At block 306, the method 300 includes generating, via a user interface, a notification that prompts the person to answer at least one verification question. For example, in an aspect, computer device 200, processor 205, memory 210, entry authorization component 215, and/or generating component 230 may be configured to or may comprise means for generating, via interface 108, a notification that prompts the person to answer at least one verification question.

Suppose that input device 106 comprises a display with buttons or a touchscreen. Interface 108 therefore be may a visual interface that presents at least one verification question. In some aspects, the at least one verification question queries health-status information, biometric information, and/or social interactions of the person. For example, a verification question may ask whether person 102 has recently experienced frequent coughing or sneezing. Alternatively, or in addition, another verification question may ask if person 102 came in contact with an individual that is diagnosed with a particular illness (e.g., coronavirus), and/or whether the person 102 themselves has recently been diagnosed with any illness.

At block 308, the method 300 includes receiving, via the user interface, at least one user response to the at least one verification question. For example, in an aspect, computer device 200, processor 205, memory 210, entry authorization component 215, and/or receiving component 235 may be configured to or may comprise means for receiving, via interface 108, at least one user response to the at least one verification question.

For example, person 102 may enter his/her responses via a touch pad on input device 106. In some aspects, interface 108 may be audio-based. Accordingly, the at least one verification question may be outputted audibly and person 102 may provide verbal user responses. Based on the example verification questions provided above, person 102 may state that he/she has not coughed/sneezed, and/or has not come in contact with an ill individual and/or has not been diagnosed with an illness.

In some aspects, if person 102 is a regular visitor that accesses checkpoint 104, computing device 200 may transmit the at least one verification question to a personal/work device of person 102. For example, the device may a smartphone or a healthy badge. By transmitting the verification questions ahead of time, when person 102 arrives at checkpoint 104, the request to gain entry through checkpoint 104 may also comprise responses to the verification questions. For example, at a time prior to accessing checkpoint 104, person 102 may answer the questions and upload the responses to computing device 200 via a wired and/or wireless communication link. Person 102 may be sent the verification questions periodically (e.g., daily, weekly, whenever person 102 is scheduled to come, etc.). This expedites the process of entry authorization.

At block 310, the method 300 includes determining whether the at least one user response and the body surface temperature match criteria for gaining entry through the checkpoint. For example, in an aspect, computer device 200, processor 205, memory 210, entry authorization component 215, and/or determining component 240 may be configured to or may comprise means for determining whether the at least one user response and the body surface temperature match criteria for gaining entry through the checkpoint.

For example, determining component 240 may determine whether the estimated body surface temperature is less than a maximum temperature of the criteria. Furthermore component 240 may compare the at least one user response to an acceptable response associated with granting entry and/or to an unacceptable response associated with denying entry. The criteria and its attributes (e.g., maximum temperature, acceptable responses, unacceptable responses, etc.) may be stored in memory 210. Suppose that the maximum temperature is 99 degrees Fahrenheit. If person 102 has a body surface temperature below or at 99 degrees, determining component 240 may determine that he/she can potentially be allowed through checkpoint 104. Furthermore, if none of the user responses match with unacceptable responses (e.g., person 102 did meet with an ill individual or person 102 has experienced recent coughing), determining component 240 may confirm that person 102 should be granted entry. In some aspects, if at least one of these attributes of person 102 (i.e., body surface temperature and user responses) is deemed unacceptable, determining component 240 may determine that person 102 should not be granted entry.

In response to determining that the at least one user response and the body surface temperature match the criteria, at 312, the method 300 includes granting the request for entry. For example, in an aspect, computer device 200, processor 205, memory 210, entry authorization component 215, and/or granting/denying component 245 may be configured to or may comprise means for granting the request.

For example, granting/denying component 245 may generate a visual indicative of a grant on interface 108. The visual may be a green light or an unlocking icon. If interface 108 is audio-based, granting/denying component 245 may output a sound indicative of a grant (e.g., a bell sound).

At block 314, the method 300 includes unlocking the checkpoint. For example, in an aspect, computer device 200, processor 205, memory 210, entry authorization component 215, and/or granting/denying component 245 may be configured to or may comprise means for unlocking checkpoint 104. For example, granting/denying component 245 may transmit an instruction, command, and/or signal to the locking mechanism of checkpoint 104 to unlock.

In contrast, in response to determining that the at least one user response and the body surface temperature do not match the criteria, at 316, the method 300 includes denying the request for entry. For example, in an aspect, computer device 200, processor 205, memory 210, entry authorization component 215, and/or granting/denying component 245 may be configured to or may comprise means for denying the request.

For example, granting/denying component 245 may generate a visual indicative of a denial on interface 108. The visual may be a red light or a locking icon. If interface 108 is audio-based, granting/denying component 245 may output a sound indicative of a grant (e.g., a buzzer sound).

At block 318, the method 300 includes transmitting an alert to initiate an additional screening of the person and denying the request. For example, in an aspect, computer device 200, processor 205, memory 210, entry authorization component 215, and/or transmitting component 250 may be configured to or may comprise means for transmitting an alert to initiate an additional screening of the person and denying the request.

For example, transmitting component 250 may transmit the alert to a device used by an official that monitors checkpoint 104. The official may be a security guard or a health professional. In some aspects the additional screening may comprise additional questions or medical tests to confirm whether person 102 should be granted or denied access through checkpoint 104, and/or these additional questions may be output to person 102 and the responses received by input device 106.

Figure 4:
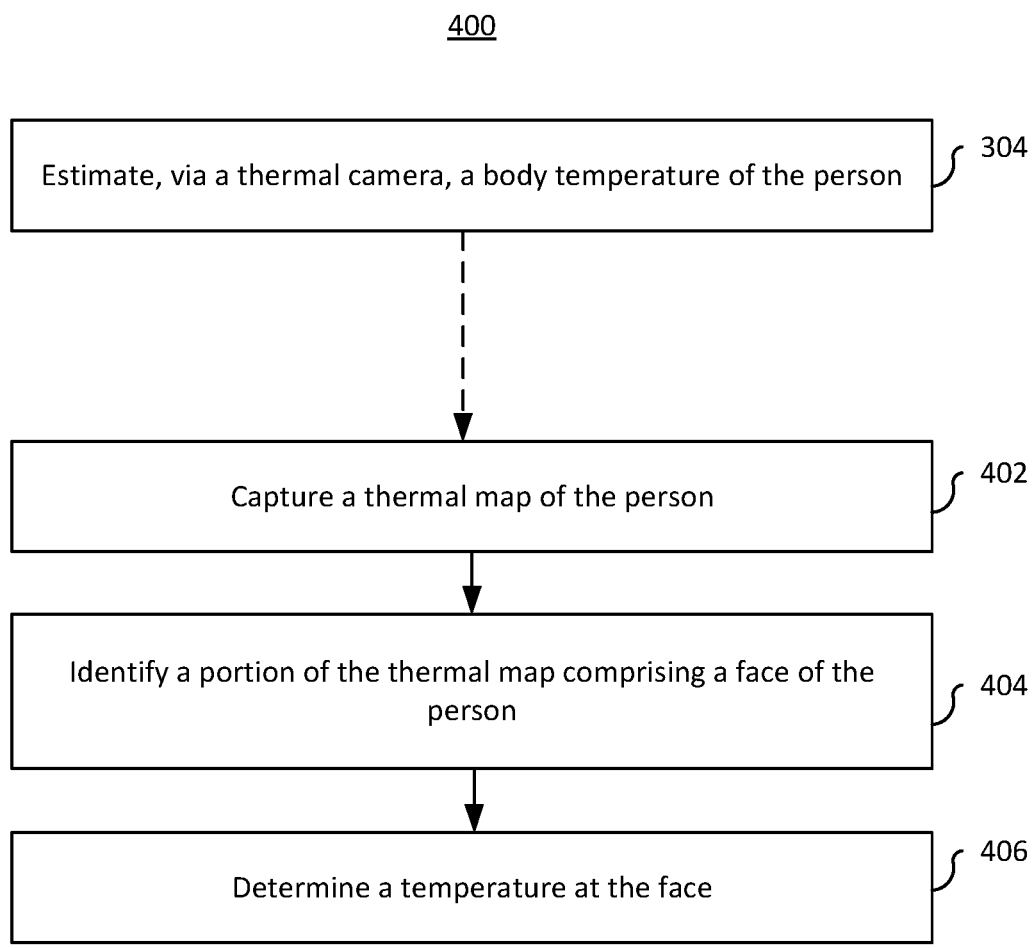
FIG. 4 is a flowchart illustrating a method of estimating body surface temperature, in accordance with exemplary aspects of the present disclosure.

FIG. 4 is a flowchart illustrating method 400 of estimating body surface temperature, in accordance with exemplary aspects of the present disclosure.

At block 402, the method 400 includes capturing a thermal map of the person. For example, in an aspect, computer device 200, processor 205, memory 210, entry authorization component 215, and/or capturing component 251 may be configured to or may comprise means for capturing a thermal map of person 102.

At block 404, the method 400 includes identifying a portion of the thermal map comprising a face of the person. For example, in an aspect, computer device 200, processor 205, memory 210, entry authorization component 215, and/or identifying component 252 may be configured to or may comprise means for identifying a portion of the thermal map comprising a face of the person. For example, the identifying at block 404 may include utilizing facial recognition software to identify the face of person 102.

At block 406, the method 400 includes determining a temperature at the face. For example, in an aspect, computer device 200, processor 205, memory 210, entry authorization component 215, and/or determining component 253 may be configured to or may comprise means for determining a temperature at the face.

For example, the determining at block 406 may include determining the average temperature represented by the pixels in the thermal map bounded by the face of person 102. More specifically, identifying component 252 may identify a plurality of thermal points in the identified portion of the thermal map (i.e., at the face). Determining component 253 may then determine an average temperature of the plurality of thermal points. Suppose that the plurality of thermal points are all the pixels within a facial boundary (e.g., from one ear to another and from the top of the forehead to the chin), where each pixel is assigned a temperature. Determining component 253 may take an average temperature of all pixels within in this boundary.

body surface temperature body surface temperature In some aspects, identifying component 252 may identify only a select few points in the portion of the thermal map. These points may be predetermined (e.g., center of the forehead, center of each cheek, chin, etc.). Determining component 253 may then determine the average temperature associated with those points. This reduces the amount computation required determining each average.

In some aspects, because the thermal map represents the external body surface temperature of person 102 and evaluating illness is conventionally based on internal body surface temperature, estimating component 225 may convert the output of thermal sensor 110 to an internal value. For example, estimating component 225 may add a few degrees to the external body surface temperature because the internal body surface temperature is normally greater than the external body surface temperature of a human.

In some aspects, the body surface temperature may be a function of the environmental temperature, the external body surface temperature of person 102 (at the face), and an amount of time person 102 has spent in the environment where checkpoint 104 is located. For example, if checkpoint 104 is located outdoors and person 102 is exposed to the sun for more than five minutes, the detected body surface temperature of person 102 may be a lot higher than his/her actual core body temperature. Estimating component 225 may thus determine a temperature adjustment that would simulate what the body surface temperature of person 102 would be at room temperature indoors. Estimating component 225 may utilize a machine learning algorithm that is trained using a dataset that includes an environmental temperature, a time spent in the environment, and a temperature adjustment. Estimating component 225 may thus retrieve the environmental temperature and request an input from the user asking how long the user was in the environment (e.g., outside prior to entering the building). Suppose that the person was outside for five minutes and the outdoor temperature is 100 degrees Fahrenheit. This may raise the skin temperature of the person. The temperature adjustment may be a decrease of 0.5 degrees Fahrenheit, as determined by estimating component 225. Thus, even if the body surface temperature is measured as 100 degrees Fahrenheit (which may normally trigger an entry denial or additional health checks), the adjustment reduces the body surface temperature to 99.5 degrees Fahrenheit (which may not trigger an entry denial).

Figure 5:
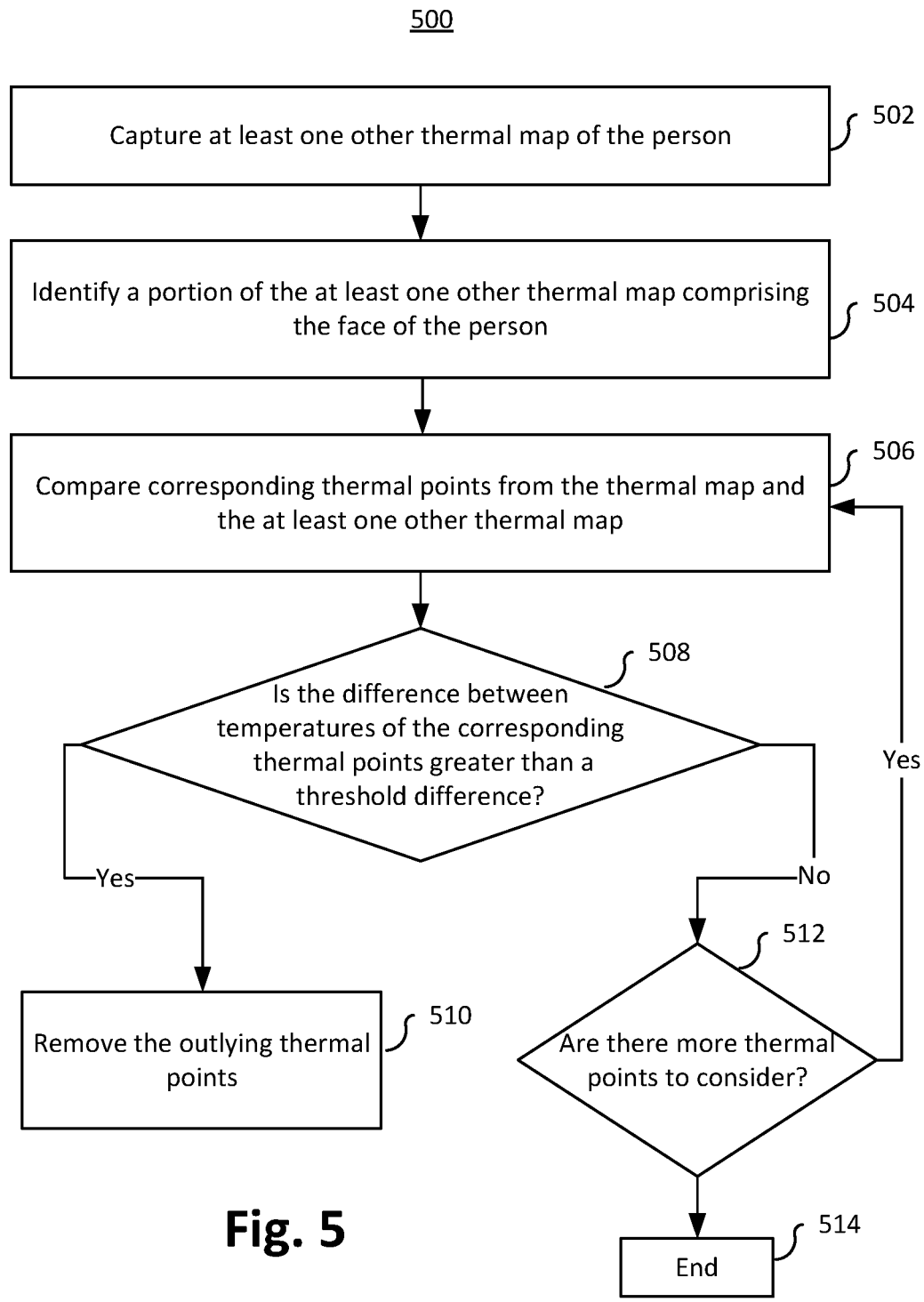
FIG. 5 is a flowchart illustrating a method of removing outlying thermal points, in accordance with exemplary aspects of the present disclosure.

FIG. 5 is a flowchart illustrating method 500 of removing outlying thermal points, in accordance with exemplary aspects of the present disclosure. At times a thermal sensor may output different temperature readings of the same point. In order to determine a consistent body surface temperature, multiple thermal maps may be captured and outlying thermal points within the thermal map may be removed.

At block 502, the method 500 includes capturing at least one other thermal map of the person. For example, in an aspect, computer device 200, processor 205, memory 210, entry authorization component 215, and/or capturing component 251 may be configured to or may comprise means for capturing at least one other thermal map of person 102.

At block 504, the method 500 includes identifying a portion of the at least one other thermal map comprising a face of the person. For example, in an aspect, computer device 200, processor 205, memory 210, entry authorization component 215, and/or identifying component 252 may be configured to or may comprise means for identifying a portion of the at least one other thermal map comprising the face of the person. For example, the identifying at block 404 may include utilizing facial recognition software to identify the face of person 102.

At block 506, the method 500 includes comparing corresponding thermal points from the thermal map originally captured and the at least one other thermal map. For example, in an aspect, computer device 200, processor 205, memory 210, entry authorization component 215, and/or comparing component 254 may be configured to or may comprise means for comparing corresponding thermal points from the thermal map originally captured and the at least one other thermal map (specifically in the facial region).

For example, at time t1, capturing component 251 may capture a first thermal map. At time t2, capturing component 251 may capture a second thermal map. Comparing component 254 may utilize facial recognition techniques to select a matching point from each thermal map. For example, matching/corresponding points may be the center of a forehead, the tip of a nose, the center of a cheek, etc.

It should be understood that while the above discussion identifies a face of person 102, another body part may be identified and utilized to derive the body surface temperature (and may use a same or a different adjustment function depending on a relationship between the body part temperature and a body surface temperature).

At block 508, the method 500 includes determining whether the difference between temperatures of the corresponding thermal points is greater than a threshold difference. For example, in an aspect, computer device 200, processor 205, memory 210, entry authorization component 215, and/or comparing component 254 may be configured to or may comprise means for determining whether the difference between temperatures of the corresponding thermal points is greater than a threshold difference.

Suppose that comparing component 254 identifies the center of a forehead identified in the first thermal map and the center of a forehead identified in the second thermal map. Comparing component 254 may determine that the associated temperatures of those points are 95 degrees Fahrenheit and 99 degrees Fahrenheit. Thus, the difference between the two corresponding thermal points is 4 degrees. Comparing component 254 may then compare this difference to a threshold difference, which is a predetermined determined value (e.g., 1.5 degrees Fahrenheit) stored in memory 210. In this example, because 4 degrees exceeds the threshold difference, comparing component 254 may determine that these thermal points are outlying thermal points. Accordingly, method 500 advances to block 510.

At block 510, the method 500 includes removing the outlying thermal points from a plurality of thermal points used to calculate an average body surface temperature. For example, in an aspect, computer device 200, processor 205, memory 210, entry authorization component 215, and/or filtering component 255 may be configured to or may comprise means for removing the outlying thermal points.

If at block 508 comparing component 254 determines that the difference is not greater than the threshold difference, the corresponding thermal points are kept in the plurality of thermal points, which are later used to determine an average body surface temperature. In this case, method 500 advances to block 512, where comparing component 254 may determine whether there are other thermal points in the plurality of thermal points that need to be compared. The loop between blocks 506 and 512 lasts until all corresponding thermal points have been compared. Subsequently, method 500 ends at block 514. It should be noted that after the plurality of thermal points in the thermal map have been filtered, determining component 253 may determine the average temperature of all remaining points in the plurality of thermal points.

While the foregoing disclosure discusses illustrative aspects and/or embodiments, it should be noted that various changes and modifications could be made herein without departing from the scope of the described aspects and/or embodiments as defined by the appended claims. Furthermore, although elements of the described aspects and/or embodiments may be described or claimed in the singular, the plural is contemplated unless limitation to the singular is explicitly stated. Additionally, all or a portion of any aspect and/or embodiment may be utilized with all or a portion of any other aspect and/or embodiment, unless stated otherwise.

What is claimed is:

1. A method for granting entry through a checkpoint, comprising:
   receiving a request for entry of a person through a checkpoint;
   in response to receiving the request for entry:
      estimating, via a thermal sensor, a body surface temperature of the person by:
         capturing a thermal map of the person, wherein the thermal map comprises a plurality of thermal points;
         capturing at least one other thermal map of the person;
         comparing the plurality thermal points of the thermal map and thermal points of the at least one other thermal map;
         identifying, based on the comparing of the thermal points, outlying thermal points that differ in temperature by more than a threshold amount;
         removing the outlying thermal points from the plurality of thermal points;
         determining the body surface temperature based on an average temperature of remaining ones of the plurality of thermal points; and
      generating, via a user interface, a notification that prompts the person to answer at least one verification question;
   receiving, via the user interface, at least one user response to the at least one verification question;
   determining whether the at least one user response and the body surface temperature match criteria for gaining entry through the checkpoint; and
   in response to determining that the at least one user response and the body surface temperature match the criteria, granting the request for entry.

2. The method of claim 1, wherein granting the request for entry comprises unlocking the checkpoint.

3. The method of claim 1, further comprising:
   in response to determining that the user response and the body surface temperature do not match the criteria, transmitting an alert to initiate an additional screening of the person and denying the request.

4. The method of claim 1, wherein determining whether the at least one user response and the body surface temperature match the criteria comprises:
   determining that the body surface temperature is less than a maximum temperature of the criteria; and
   comparing the at least one user response to an acceptable response associated with granting entry and/or to an unacceptable response associated with denying entry.

5. The method of claim 1, wherein receiving the request for entry comprises receiving entry credentials of the person via a scanning device at the checkpoint, wherein the scanning device is configured to capture at least one of: a fingerprint, a facial image, a retina scan, a vocal input, an identify card barcode, a QR code, or electronic identification information from a device of the person.

6. The method of claim 1, wherein estimating the body surface temperature of the person further comprises:
   identifying a portion of the thermal map comprising a face of the person, wherein a first subset of the plurality of thermal points are solely within the face of the person;
   identifying another portion of the at least one other thermal map comprising the face of the person, wherein a second subset of the thermal points of the at least one other thermal map are solely within the face of the person;
   wherein comparing the plurality thermal points of the thermal map and thermal points of the at least one other thermal map comprises comparing the first subset and the second subset;
   wherein identifying the outlying thermal points is based on the comparing of the first subset and the second subset;
   wherein removing the outlying thermal points includes removing from the first subset and/or the second subset; and
   determining a temperature at the face based on remaining ones of the first subset and the second subset, wherein the temperature at the face is set as the body surface temperature of the person.

7. The method of claim 1, wherein the at least one verification question queries biometric information and social interactions of the person.

8. An apparatus for granting entry through a checkpoint, comprising:
   a thermal sensor;
   a memory; and a processor in communication with the memory and configured to:
- receive a request for entry of a person through a checkpoint;
- in response to receiving the request for entry:
  - estimate, via the thermal sensor, a body surface temperature of the person;
    - capturing a thermal map of the person, wherein the thermal map comprises a plurality of thermal points;
    - capturing at least one other thermal map of the person;
    - comparing the plurality thermal points of the thermal map and thermal points of the at least one other thermal map;
    - identifying, based on the comparing of the thermal points, outlying thermal points that differ in temperature by more than a threshold amount;
    - removing the outlying thermal points from the plurality of thermal points;
    - determining the body surface temperature based on an average temperature of remaining ones of the plurality of thermal points; and
  - generate, via a user interface, a notification that prompts the person to answer at least one verification question;
- receive, via the user interface, at least one user response to the at least one verification question;
- determine whether the at least one user response and the body surface temperature match criteria for gaining entry through the checkpoint; and
- in response to determining that the at least one user response and the body surface temperature match the criteria, grant the request for entry.

9. The apparatus of claim 8, wherein the processor is further configured to grant the request for entry by unlocking the checkpoint.

10. The apparatus of claim 8, wherein the processor is further configured to:
- in response to determining that the user response and the body surface temperature do not match the criteria, transmit an alert to initiate an additional screening of the person and denying the request.

11. The apparatus of claim 8, wherein the processor is further configured to determine whether the at least one user response and the body surface temperature match the criteria by:
- determining that the body surface temperature is less than a maximum temperature of the criteria; and
- comparing the at least one user response to an acceptable response associated with granting entry and/or to an unacceptable response associated with denying entry.

12. The apparatus of claim 8, further comprising a scanning device, wherein the processor is further configured to receive the request for entry by receiving entry credentials of the person via the scanning device at the checkpoint, wherein the scanning device is configured to capture at least one of: a fingerprint, a facial image, a retina scan, a vocal input, an identify card barcode, a QR code, or electronic identification information from a device of the person.

13. The apparatus of claim 8, wherein the processor is further configured to estimate the body surface temperature of the person by:
- identifying a portion of the thermal map comprising a face of the person, wherein a first subset of the plurality of thermal points are solely within the face of the person;
- identifying another portion of the at least one other thermal map comprising the face of the person, wherein a second subset of the thermal points of the at least one other thermal map are solely within the face of the person;
- wherein comparing the plurality thermal points of the thermal map and thermal points of the at least one other thermal map comprises comparing the first subset and the second subset;
- wherein identifying the outlying thermal points is based on the comparing of the first subset and the second subset;
- wherein removing the outlying thermal points includes removing from the first subset and/or the second subset; and
- determining a temperature at the face based on remaining ones of the first subset and the second subset, wherein the temperature at the face is set as the body surface temperature of the person.

14. A non-transitory computer-readable medium for granting entry through a checkpoint, executable by a processor to:
- receive a request for entry of a person through a checkpoint;
- in response to receiving the request for entry:
  - estimate, via a thermal sensor, a body surface temperature of the person by:
    - capturing a thermal map of the person, wherein the thermal map comprises a plurality of thermal points;
    - capturing at least one other thermal map of the person;
    - comparing the plurality thermal points of the thermal map and thermal points of the at least one other thermal map;
    - identifying, based on the comparing of the thermal points, outlying thermal points that differ in temperature by more than a threshold amount;
    - removing the outlying thermal points from the plurality of thermal points;
    - determining the body surface temperature based on an average temperature of remaining ones of the plurality of thermal points; and
  - generate, via a user interface, a notification that prompts the person to answer at least one verification question;
- receive, via the user interface, at least one user response to the at least one verification question;
- determine whether the at least one user response and the body surface temperature match criteria for gaining entry through the checkpoint; and
- in response to determining that the at least one user response and the body surface temperature match the criteria, grant the request for entry.

* * * * *